United States Patent
Pomerantzeff

[11] 3,944,341
[45] Mar. 16, 1976

[54] WIDE-ANGLE OPHTHALMOSCOPE AND FUNDUS CAMERA

[75] Inventor: Oleg Pomerantzeff, Brookline, Mass.

[73] Assignee: Retina Foundation, Boston, Mass.

[22] Filed: Oct. 4, 1974

[21] Appl. No.: 512,327

Related U.S. Application Data

[63] Continuation-in-part of Ser. No. 292,150, Sept. 25, 1972.

[52] U.S. Cl. ................... 351/7; 350/96 B; 350/179; 350/220; 351/6; 351/16; 354/62
[51] Int. Cl.² .......................................... A61B 3/14
[58] Field of Search ................ 351/16, 6, 7; 354/62; 350/96 B, 179, 220

[56] References Cited
UNITED STATES PATENTS
3,770,342   11/1973   Dudragne ............................. 351/7

*Primary Examiner*—Paul A. Sacher
*Attorney, Agent, or Firm*—Kenway & Jenney

[57] ABSTRACT

A wide-angle indirect ophthalmoscope contains a contact lens that fits over a cornea and is surrounded by two rings of optical fibers for illumination of the eye fundus. The two rings of fibers are oriented to maximize illumination of the fundus while reducing troublesome reflections. The inside ring is formed of fibers with a numerical aperture and inclination selected to illuminate 100° of the retina. The outside ring of fibers illuminates the periphery of the retina up to 150°. The location and inclination of the rings are calculated to prevent blockage of the entrance pupil of the observation system while avoiding direct illumination of the entrance pupil.

A lens series for use in an ophthalmoscope in combination with the contact lens is also disclosed.

Further, a fundus camera contains the contact lens, the two rings of optical fibers, and a lens series for use in conjunction with a camera having a 50 mm focal length.

21 Claims, 7 Drawing Figures

WIDE-ANGLE OPHTHALMOSCOPE AND FUNDUS CAMERA

CROSS REFERENCE TO RELATED APPLICATION

This application is a continuation-in-part of my earlier co-pending application Ser. No. 292,150, filed Sept. 25, 1972, entitled Wide-Angle Ophthalmoscope.

BACKGROUND OF THE INVENTION

The present invention relates to instruments which are used to examine and to photograph the interior of an eye, and which are known as ophthalmoscopes and fundus cameras respectively. The present instruments are an improvement in those ophthalmoscopes and fundus cameras disclosed in my co-pending patent application Ser. No. 292,150, filed Sept. 25, 1972, entitled Wide-Angle Ophthalmoscope, the teachings of which are incorporated herein by reference.

In my earlier co-pending application, an ophthalmoscope and a fundus camera are disclosed which include optical fibers built into a contact lens in a circular pattern to form a single ring of optical fibers around the contact lens. The importance of maintaining a single circular pattern of fibers in a predetermined fixed orientation in relationship to the contact lens is emphasized. For a single ring of fibers having a numerical aperture of 0.66 or greater, it was found advantageous to orient the ring so that the fibers made an angle of 25°–35° with the axis of the lens. With an ophthalmoscope or fundus camera containing that single ring of high numerical aperture optical fibers, it is possible to illuminate 100° of the fundus. However, the field of illumination can not be increased further when conventional optical fibers are utilized, without deleterious effects. It is of course desirable to increase the field of illumination, and accordingly increase the field of view that is possible without scanning.

SUMMARY OF THE INVENTION

In accordance with the present invention, a fundus camera or ophthalmoscope results which illuminates 150° of an eye fundus with conventional optical fibers of comparitively low numerical aperture and enables a field of view of 150°, all without scanning. Both instruments include a contact lens capable of being placed on a patient's cornea and surrounded by two distinct rings of optical fibers. The orientation and the numerical aperture of the optical fibers forming the rings are calculated so that a maximum area of the eye fundus is illuminated without having light from the optical fibers strike the front surface of the entrance pupil of the eye to be examined.

Accordingly, it is an object of the present invention to provide an ophthalmoscope and a fundus camera, each of which is capable of viewing or photographing an eye fundus with a field of view of approximately 150° using conventional optical fibers as the illumination source.

DESCRIPTION OF THE PREFERRED EMBODIMENTS

The present invention is directed to fundus cameras and ophthalmoscopes. Ophthalmoscopes are used for visual examination of an eye fundus; whereas, fundus cameras are used to photograph an eye fundus.

The wide-angle ophthalmoscopes and fundus cameras of the present invention include fiber optic light guides having their exit ends arranged in two rings for illuminating the retina. The two illuminating rings function in conjunction with a contact lens to provide a wide-angle view of the field which is uniformly illuminated by the fiber optic light guides. An important aspect of the present invention is the location of the two illuminating rings of fibers, the inclination of the fibers at the contact point with the cornea and the numerical aperture of the fibers.

Several components of the ophthalmoscope and of the fundus camera of the present invention are similar. A common feature found in both the fundus camera (FIG. 1) and the ophthalmoscope (FIG. 4) is the contact lens 10' and 10 of fundus camera 12 and ophthalmoscope 14. Other common components which are characteristic to each instrument are the two rings of optical fibers 16' and 18' of fundus camera 12 and rings 16 and 18 of ophthalmoscope 14.

Preferably contact lens 10', 10 (which is also designated in FIG. 7 as lens I) is formed of a glass which is sold by the Eastman Kodak Company, 901 Elm Grove Road, Rochester, N.Y. under their designation EK–911. This glass has a refractive index ($n_d$) of 2.1. Another glass which is suitable for forming contact lens 10', 10 is sold by Jenaer Glaswerk Schott & Gen., Mainz, West Germany, (hereinafter called Schott) under their designation LaSF 6 – 961349. This glass has a refractive index ($n_d$) of 1.96052. Other constructional parameters for lens 10', 10 are given in Table I below. As used throughout this specification and claims, R indicates the radius of curvature, T indicates the thickness of the lens, and S indicates the distance between opposed lens surfaces.

TABLE I

| Lens | Radius, R | Thickness, T | Refractive Index, $n_d$ | Space, S | Abbe number (dispersion) |
|---|---|---|---|---|---|
| I | $R_1$ = 8.2 mm<br>$R_2$ = 10.2 mm | $T_1$ = 9.2 mm | 2.1 | $S_1$ = 4.0 mm | 25.6 |

Contact lens 10, 10' (I) is a concavo-convex singlet lens which is a positive focusing lens when placed on a cornea.

Figure 1:
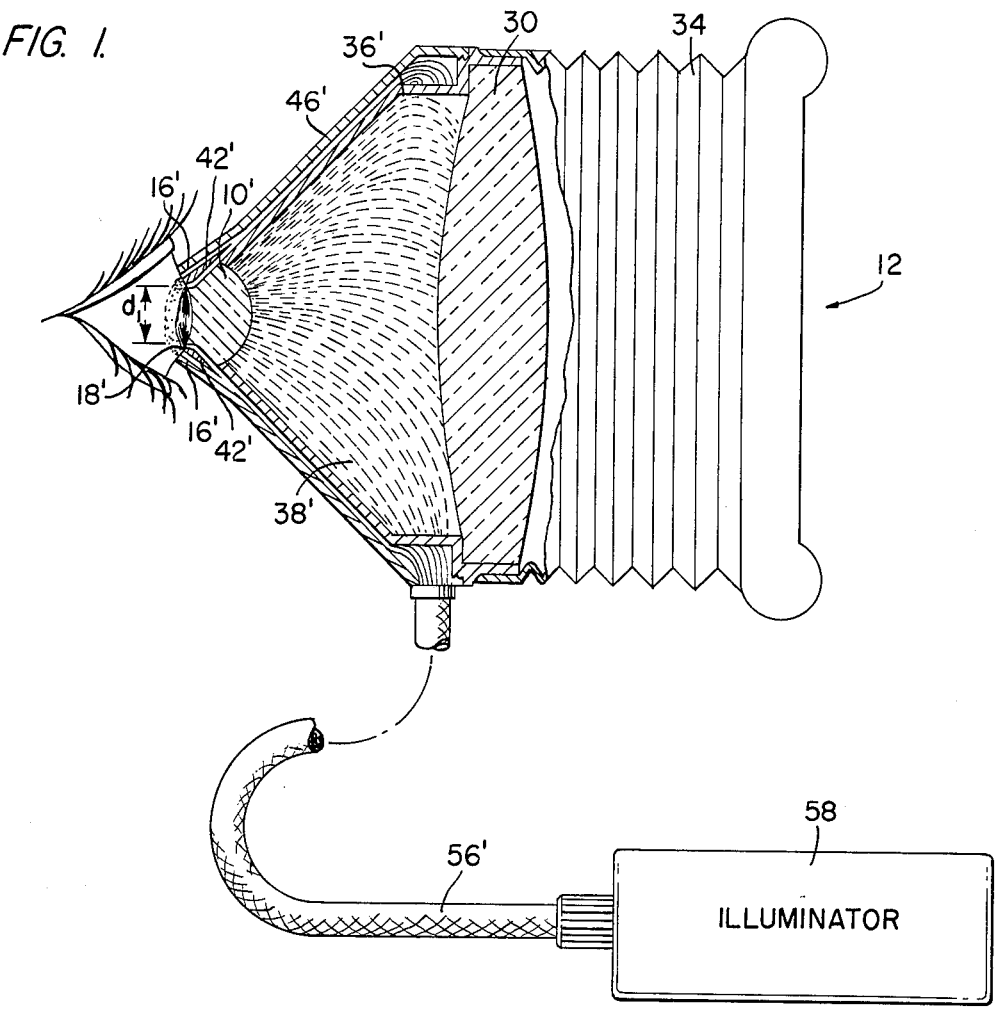
FIG. 1 is a schematic view partially in section of a fundus camera in accordance with the present invention.

The diameter $d_1$ of the portion of contact lens 10, 10' that contacts the cornea (as is shown in FIG. 1) is 8 mm. The operable range of this diameter $d_1$ of the forward surface of contact lens 10', 10 is 7-8 mm. At this point it is emphasized that any dimensions given in the specification are optimized to be compatible with an average eye. However, as will be apparent to those skilled in this art, the parameters of the ophthalmoscope and of the fundus camera may be varied so that the instruments can be utilized on a patient whose eyes deviate in size from an average eye. A case where such deviation is noteworthy is the case of small children. However, from the present specification, one skilled in the art is provided with all the information necessary to make whatever corrections are necessary to provide an ophthalmoscope or fundus camera in accordance with the general concepts of the present invention and which can be effectively utilized to examine and to photograph the retinas of children or any other patients having eyes which deviate from an average eye.

As is set forth above, the instruments of the present invention employ optical fibers for illuminating the retina. Optical fibers 38 (FIG. 4) operate on the principle of total internal reflection. This principle is so well known that it requires only a brief description. A transparent elongated smooth surfaced body of higher refractive index than its surroundings can transmit light applied to one end so that it emerges with little loss at the other end, due to total internal reflection from its surfaces of light rays divergent from the longitudinal axis of the body. To produce total internal reflection within each fiber, each fiber is formed of a central glass core surrounded by a thin sheath or cladding of glass having a lower refractive index than the core. Although glass fibers are preferred, the light guiding fibers may be formed of transparent plastics. However, the construction of light guiding fibers from either glass or plastic is well within the skill of those in this art. Since the optical fibers used in the present instruments do not tranmit an image, but only are used for illuminating the retina, the fibers are not arranged to be coherent.

One important embodiment of the present invention utilizes clad fibers with a numerical aperture (N.A.) of 0.55.

A major difference between the ophthalmoscope and the fundus camera of the present invention and the ophthalmoscope and the fundus camera disclosed in U.S. patent application Ser. No. 292,150 is that instruments constructed in accordance with the present invention include two rings of optical fibers, an outside ring 16', 16 and an inside ring 18', 18; whereas, in my prior application only one ring is disclosed. In the illustrated embodiments of FIGS. 1 and 4, inside ring 18', 18 abuts against and encircles contact lens 10', 10. Thus, the inside diameter of ring 18', 18 is 8 mm. The ring is approximately 0.5 mm thick. Thus, the outside diameter of ring 18', 18 is 9 mm. Outside ring 16', 16 is separated from inside ring 18', 18 a distance of about 0.5 mm. Thus, the inside diameter of outside ring 16', 16 is 10 mm. The ring formed by the outer optical fibers is approximately 1 mm thick; therefore, the outside diameter of outside ring 16', 16 is 12 mm.

Figure 2:
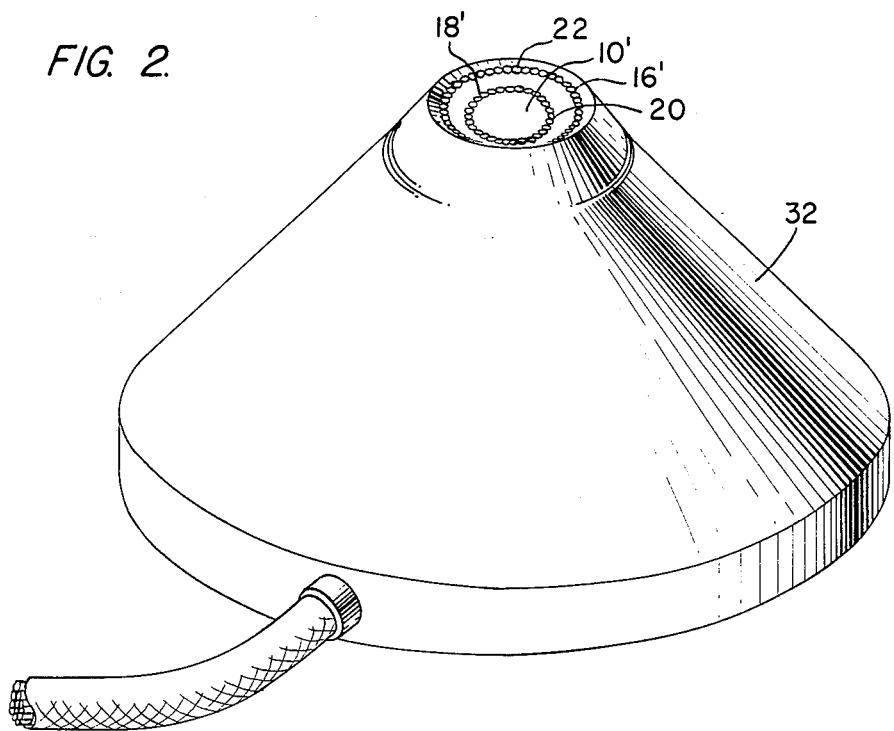
FIG. 2 is a perspective view of an illuminating cone in accordance with the present invention for use in conjunction with a fundus camera.

At this point, it should be noted that the rings 16' and 18' shown in FIG. 2 shows fibers that are greatly exaggerated in size. The individual fibers which form the rings of fibers may be only 0.002 inches in diameter.

Figure 6:
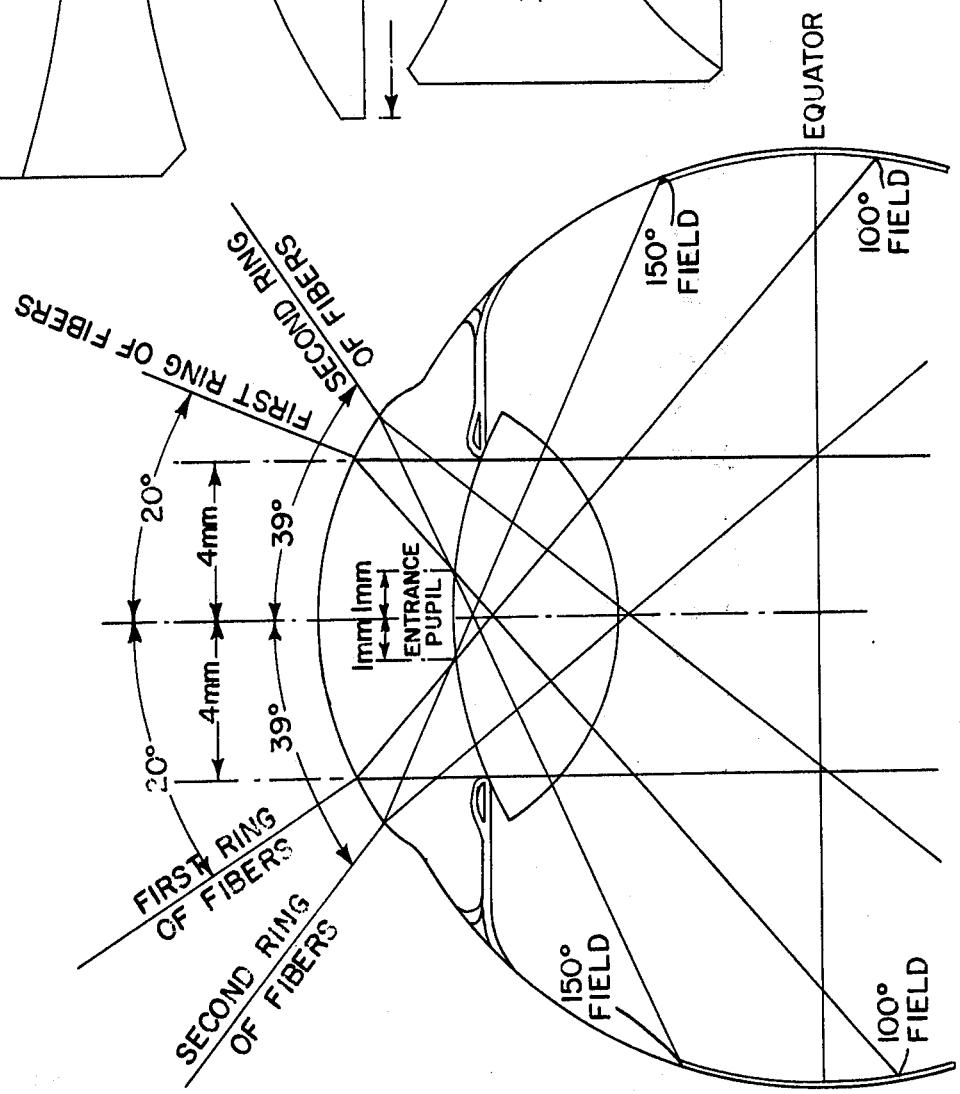
FIG. 6 is a diagram illustrating the illumination of a retina with two rings of fibers in accordance with the present invention; and, FIG. 7 is a cross-sectional view of a lens series for use in a fundus camera in accordance with the present invention.

In accordance with the present invention, when fibers 38 have a numerical aperture of 0.55, the tips 20 of the optical fibers which form ring 18,18' make an angle with the axis of the lens which is between the range of 18° to 24°. Preferably, as FIG. 6 shows the tips of fibers 20 make an angle of 20° with the axis of lens 10, 10'.

The tips 22 of the fibers which form ring 16, 16' make an angle with the axis of the lens, 10, 10' which is between the range of 35°-42°. Preferably tips 22 make an angle of 39° with the axis of lens 10,10' when fibers with a numerical aperature of 0.55 are utilized. The significance of the foregoing orientation of rings 16', 16 and 18', 18 as well as a convenient method for maintaining the position of these rings inside the ophthalmoscope and fundus camera are disclosed below.

Figure 4:
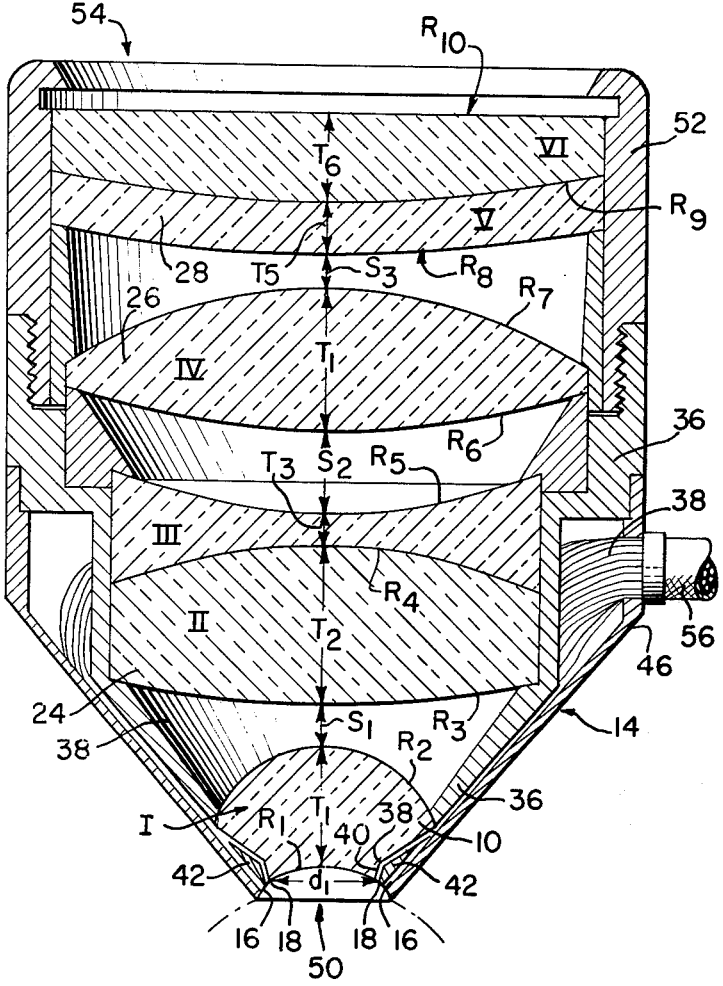
FIG. 4 is a cross-sectional view of an ophthalmoscope in accordance with the present invention.
Figure 7:
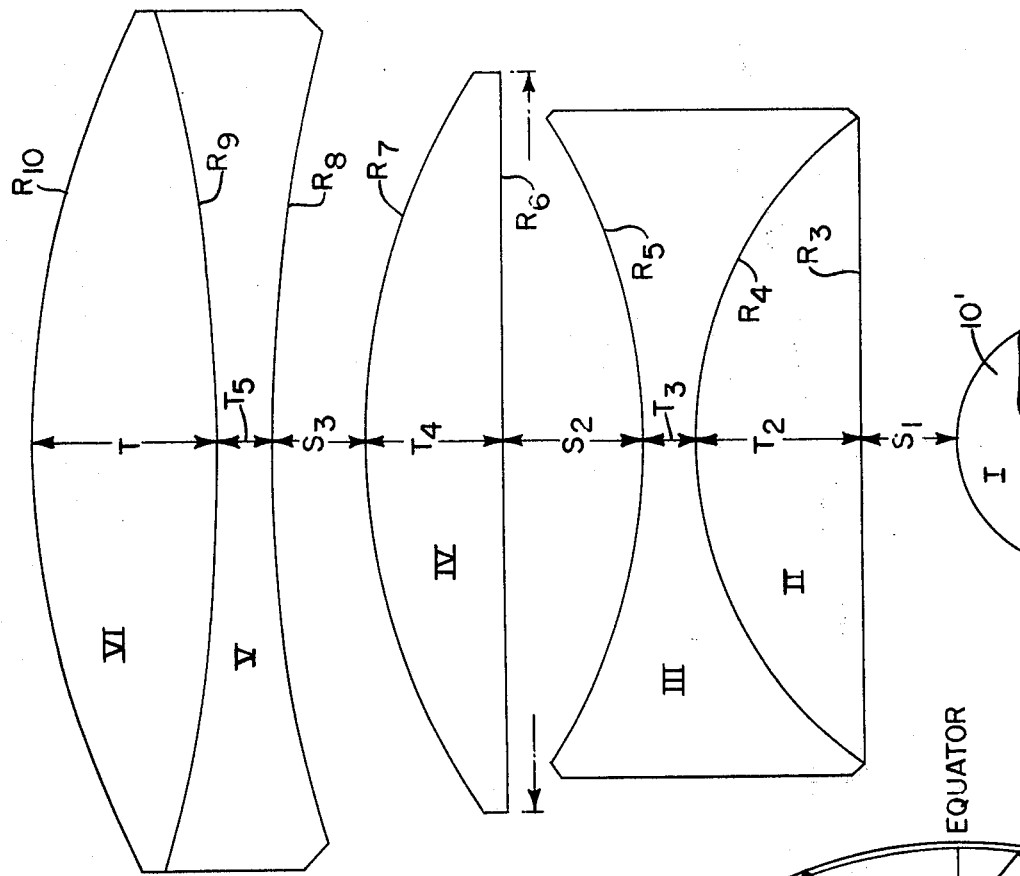

At this point it should be noted that the major difference between the ophthalmoscope 14 and the fundus camera 12 is that with an opthalmoscope, lenses 24, 26, and 28 (II-VI) in FIGS. 4 and 7 are built directly into the instrument; whereas, in the case of a fundus camera, a corresponding lens series, representing schematically as lens 30 in FIG. 1, is positioned between the illuminating cone 32 and a camera 34.

Figure 3:
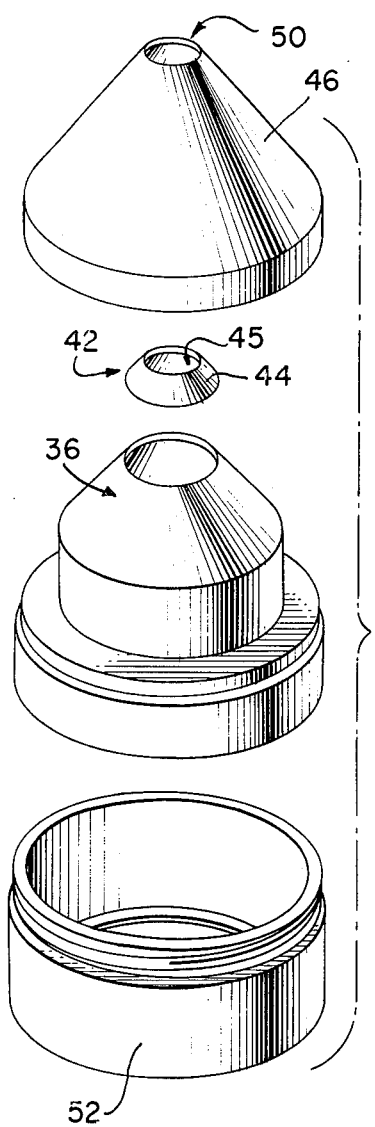
FIG. 3 is an exploded perspective view of several components of an ophthalmoscope in accordance with the present invention.

A convenient method for maintaining the required positioning of the rings of optical fibers is set forth below with reference to FIGS. 3 and 4. The $R_2$ surface of lens 10 is cemented to the forward end of a lens mount 36. Optical fibers 38 are fanned over mount 36 and the side of lens 10 to forming a circular, conical array of fibers which is cemented to the lens with an opaque epoxy. As also shown, the outer upper surface of lens 10 is designed with a geometric configuration such that the terminal ends of fibers 38 make an angle between the range of 18°-24° with the axis of lens 10. Of course, the lens mount 36 is preferably shaped so that the angle is 20° for fibers with a numerical aperture of 0.55. Thereafter, a separator 42 is placed down on the lens and circular array of fibers which forms ring 18. Separator 42 is fabricated so that it has a conically tapered outer surface 44 which makes an angle of 35°-42° (preferably 39°) with the axis of lens 10, with the inner surface 45 being inclined at an angle to correspond to the angle of the tips of fibers forming ring 20. After separator 42 is positioned in place, fibers 38 are fanned over the tapered outer surface of separator 42 to form a circular array and cemented thereto. Thereafter, a cone member 46 is added to secure the foregoing assembly. Cone member 46 may be cemented to lens mount 36; or, these component may be secured together by a friction fit. It has also been found advantageous to cover the fanned arrays of fibers with an opaque epoxy cement to secure them to the contact lens and lens support, or to the separator, as the case may be. The epoxy may also be used to cement cone 46 to lens mount 36. The forward end 50 of the foregoing arrangement is ground to expose the two rings of optical fibers and to yield a contact lens 10 which has a configuration which enables it to be placed on a cornea. The ophthalmoscope also includes a lens holder member 52 which is used to hold lens 28 and which is screwed into lens mount 36. Lens mount 36, separator 42, cone member 46, and lens holder member 52 are preferably formed of a corrosion resistant metal. In use a viewer observes the eye fundus by looking into rearward end 54. The image of the fundus may be enlarged by placing an appropriate field lens (not shown) between the rearward end 54 and the observer.

It should be apparent that the illuminating cone 32 of fundus camera 12 (FIG. 1) can be fabricated in a similar fashion by cementing lens 10' to a lens mount 36', laying fibers over the lens 10', adding a separator 42', laying fibers over the separator 42', and then adding a cone member 46'.

The fibers 38, 38' leave the instruments through an opening formed in cone member 46, 46' whereupon they form a cable 56, 56' which is plugged into a conventional fiber optic illuminator. Thus, light from the illuminator 58 (FIG. 1) is conducted through cable 56, 56' and into the instruments for illumination of the patient's retina. For best results, it has been discovered that the optical fibers in cable 56, 56' should be the same fibers as those used in the instrument, i.e., fibers 38, 38'.

The instruments of the present invention are constructed not ony to be compatible with the organs in the eye, but also to utilize such organs to maximum advantage. For example, the field of view of a normal individual extends temporily to at least 90° of arc. This means that the rays emitted toward the observer's pupil by all the points in a field of about 180° of arc pass through an undilated pupil and reach points in the observer's retina. Rays reaching the retina from the nasal portion of the field fall on an area of the retina that is not photosensitive. Conversely, if the retina is illuminated, its points emit rays which, when passing through an undilated pupil, contain the aerial image of the whole retina and form a solid angle of about 180° of arc. Thus, a small-pupil ophthalmoscope with an optimally corrected condensing lens permits observation of the peripheral retina through an undilated pupil. However, to view 150° of the retina in a single image, 150° of the retina must be illuminated without producing bothersome reflections, and the solid angle containing the aerial image of the fundus must be condensed to permit its simultaneous projection into the observer's retina.

In order to illuminate 150° of the retina without reflections and to condense the image of the fundus, it is advantageous to provide two rings of illuminating fibers in accordance with the present invention. The reason why it is advantageous to include the two rings of illuminating fibers will be apparent from a consideration of the optics of a cornea which is discussed in conjunction with FIGS. 5 and 6.

Figure 5:
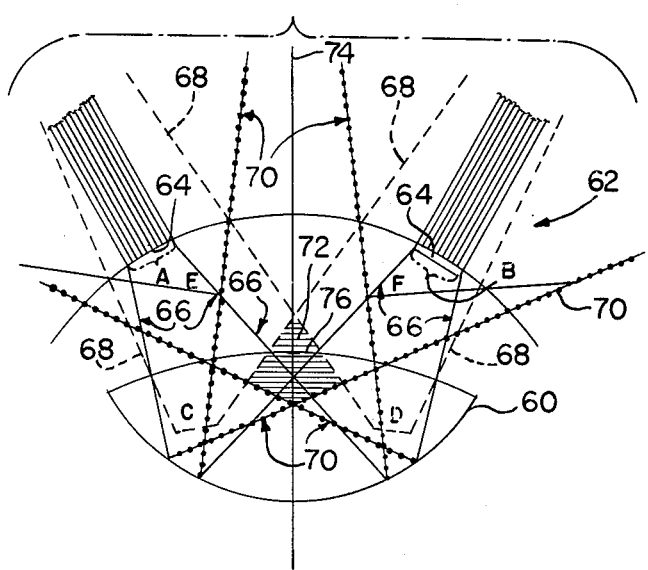
FIG. 5 is a diagram illustrating how light emerging from an optical fiber travels through an eye.

FIG. 5 is a diagram illustrating the reflection by the crystalline lens 60 of an eye 62 of light transmitted through a ring of fibers 64. Two points on ring 64 are labelled A and B. The corresponding limits of the illuminating beam are indicated by thin solid lines 66. The images points A and B formed by the front surface of the crystalline lens 60 (which is considered as a mirror) are labelled C and D. The dash lines 68 starting from images C and D show the beams carrying the reflections. The reflections from points A and B formed by the back surface of the crystalline lens 36 are labelled E and F. Corresponding beams carrying the reflections are indicated by dotted lines 70 starting from E and F. As is apparent from FIG. 5, to prevent the reflections from entering the observer's eye, the only place where the entrance pupil of the observation system can be located is in the cross-hatched area 72. Thus, the ring of fibers 64 must be placed on the patient's cornea so as not to obstruct the observation system. Ideally, ring 64 should have an inside diameter which is located 4 mm from the axis 74 of crystalline lens 60. Thus, it is seen why it is advantageous to provide a ring of illuminating fibers with an inside diameter of 8 mm.

A second consideration for optimizing the field of view and the field of illumination is the inclination of the ring of fibers 64. With high numerical aperture fibers (0.66) and with the tips of fiber 64 inclined at an angle of 30° to the axis 74, the field of illumination is about 100°. Of course, as the angle is decreased, the field of illumination will also decrease. Unfortunately, as the angle is increased, or as the numerical aperture of the fibers is increased, light emerging from ring 64 will strike the front surface 76 of crystalline lens 60, which is undesirable.

Front surface 76 is the entrance pupil for the observation system. Direct illumination of the entrance pupil will result in a reflection of the halo of light which is emitted from the ring 64 and will cause blurring of the central part of the image of the fundus. As is shown in FIG. 6, with the inside of the first ring of fibers located 4 mm from the axis of the lens and being composed of fibers with a numerical aperture of 0.55 and being inclined at an angle of 20° with the axis, 100° of field is illuminated without having light emerging from the fibers pass through the 1 mm radius entrance pupil. By placing a second ring of 0.55 N.A. fibers to form an outside ring whose inside diameter is 10 mm from the axis of the lens and which is inclined at an angle of 39° with the axis, the field of illumination is increased to 150° without having light emerging from the second ring strike the entrance pupil of the observation system.

At this point it should be noted that the angle of inclination of the fibers is determined by considering the numerical aperture of the fibers. For example, when the numerical aperture is 0.55, the optimum angle for the tips of fibers forming the inside ring is 20°. However, if fibers having a numerical aperture of 0.66 are selected, then the angle of the tip of fibers forming the inside ring need only be 12° to illuminate 100° of the field. Thus, one significance of the present invention is the recognition that the instrument contains a contact lens enclosed by an inside ring of fibers with an 8 mm diameter and with a numerical aperture and tip inclination selected to illuminate 100° of the field and leave the entrance pupil free from direct illumination, and a second ring of fibers which are positioned and angled to illuminate the periphery to about 150°, again without directly illuminating the entrance pupil.

As is stated above, the ophthalmoscope and the fundus camera includes a lens series to condense and focus the image of the fundus after it passes through the contact lens. In the case of the ophthalmoscope, the lens series is built right into the instrument as is shown in FIG. 4 and together with the contact lens 10 provides two power magnification. The lens series includes a lens 24 which is a doublet comprising a double convex lens element II which lies in surface contact with a double concave element III. A second singlet double convex lens 26 is located a distance $S_2$ from doublet 24. A doublet 28 is located a distance $S_3$ from singlet 26. Doublet 28 comprises a convex-concavo lens V in surface contact with a forward convex-concavo lens VI. The lens parameters appear in Table II below. In Table II and throughout this specification and claims a minus sign indicates radius of center or curvature lying on the object side of the corresponding vertex.

TABLE II

| Lens | Radius, R | Thickness, T | Space, S | Refractive Index | Abbe number (dispersion) |
| --- | --- | --- | --- | --- | --- |
| II | $R_3 = -3.0737$ in | $T_2 = 12$mm | | 1.85026 | 32.23 |
|  | $R_4 = 1.3780$ in | | | | |
| III | $R_5 = 1.3780$ in | $T_3 = 3$mm | $S_2 = 5$mm | 1.5168 | 64.17 |
| IV | $R_6 = -3.8189$ in | $T_4 = 10$mm | $S_3 = 4$mm | 1.4645 | 65.77 |
|  | $R_7 = 1.5645$ in | | | | |
| V | $R_8 = 4.3282$ in | $T_5 = 4$mm | | 1.5168 | 64.17 |
|  | $R_9 = 3.6830$ in | | | | |
| VI | $R_{10} = 49.6846$ in | $T_6 = 8$mm | | 1.7215 | 29.25 |

The fundus camera of FIG. 1 includes a corresponding lens series for use in conjunction with contact lens 10' and a 50mm focal length camera such as a Nikon F. This lens series together with contact lens 10' provides 1.8 magnification of the image to be photographed. The series is shown in FIG. 7 and includes a doublet comprising a biconvex lens II in surface contact with a biconcave lens III separated a distance $S_1$ from contact lens 10'. A plano-convex lens IV is separated from lens III a distance $S_2$ and a doublet formed by a biconcave lens V in surface contact with a biconvex lens VII is separated from lens IV by a distance $S_3$. The lens parameters appear in Table III below.

TABLE III

| Lens | Radius, R | Thickness, T | Space, S | Refractive Index | Abbe number (dispersion) |
| --- | --- | --- | --- | --- | --- |
| II | $R_3 = 1440.$ in | $T_2 = 20$mm | $S_1 = 23$mm | 1.85026 | 32.23 |
|  | $R_4 = 44.4$ in | | | | |
| III | $R_5 = -59.7$ in | $T_3 = 6$mm | $S_2 = 30$mm | 1.5168 | 64.17 |
| IV | $R_6 = \infty$ | $T_4 = 15$mm | $S_3 = 20$mm | 1.4645 | 65.77 |
|  | $R_7 = 66.3$ in | | | | |
| V | $R_8 = 165$ in | $T_5 = 6$mm | | 1.5168 | 64.17 |
|  | $R_9 = -169$ in | | | | |
| VI | $R_{10} = 94.8$ in | $T_6 = 20$mm | | 1.7215 | 29.25 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. An ophthalmoscope comprising a contact lens through which the interior of the eye can be viewed, said contact lens being surrounded by arrays of optical fibers to form an inside ring of optical fibers and an outside ring of optical fibers spaced apart from said inside ring, said contact lens having a configuration which enables it to be placed on a cornea, said fibers being oriented in a predetermined position to form said rings of predetermined radii, the tips of said fibers forming the rings that face a patient's cornea when the ophthalmoscope is in use making a first predetermined angle in said inside ring and a second predetermined angle in said outside ring, the numerical aperture of said fibers, the first predetermined angle of said fibers and the radius of said inside ring being selected so that said inside ring illuminates the central part of the field and leaves the entrance pupil of the observation system free from direct illumination, said second ring of fibers having a radius and being positioned and angled to illuminate the periphery of the field without directly illuminating the entrance pupil.

2. The ophthalmoscope as set forth in claim 1 wherein the inside ring has an inside diameter between the range of 7 - 8mm.

3. The ophthalmoscope as set forth in claim 1 wherein the inside ring has an inside diameter between the range of 8 mm.

4. The ophthalmoscope as set forth in claim 3 wherein the numerical aperture of said fibers is 0.55 and the first predetermined angle is 18°-24°.

5. The ophthalmoscope as set forth in claim 3 wherein the numerical aperture of said fibers is 0.55 and the first predetermined angle is 20°.

6. The ophthalmoscope as set forth in claim 4 wherein second predetermined angle is 35°-42°.

7. The ophthalmoscope as set forth in claim 5 wherein said second predetermined angle is 39°.

8. The ophthalmoscope as set forth in claim 7 wherein the outside diameter of said inside ring is 9mm, said outside ring is spaced apart a distance of 0.5mm from said inside ring and is 1mm thick.

9. The ophthalmoscope as set forth in claim 1 wherein the contact lens has a geometric shape to produce the first predetermined angle and includes a separator over the fibers forming said inside ring with fibers forming said outside ring being positioned over said separator, said separator having an outer surface tapered to produce said second predetermined angle.

10. Th ophthalmoscope as set forth in claim 1 wherein the inside ring of optical fibers abuts the surface of said contact lens that contacts a patient's cornea when in use.

11. A fundus camera comprising a cone member connected through a lens series to a camera, said cone member including a contact lens through which the interior of the eye can be photographed, said contact lens being surrounded by arrays of optical fibers to form an inside ring of optical fibers abutting the surface of said contact lens that contacts a patient's cornea when in use and an outside ring of optical fibers spaced apart from said inside ring, said contact lens having a configuration which enables it to be placed on a cornea, said fibers being oriented within said lens in a predetermined position to form said rings of predetermined radii, the tips of said fibers forming the rings that face a patient's cornea when the fundus camera is in use making a first predetermined angle in said inside ring and a second predetermined angle in said outside ring, the numerical aperture of said fibers, the first predetermined angle of said fibers and the radius of said inside ring being selected so that said inside ring illuminates the central part of the field and leaves the entrance pupil of the observation system free from direct illumination, said second ring of fibers having a radius and being positioned and angled to illuminate the periphery of the field without directly illuminating the entrance pupil.

12. The fundus camera as set forth in claim 11 wherein the inside ring has an inside diameter between the range of 7 – 8mm.

13. The fundus camera as set forth in claim 11 wherein the inside ring has an inside diameter between the range of 8mm.

14. The fundus camera as set forth in claim 13 wherein the numerical aperture of said fibers is 0.55 and the first predetermined angle is 18°–24°.

15. The fundus camera as set forth in claim 13 wherein the numerical aperture of said fibers is 0.55 and the first predetermined angle is 20°.

16. The fundus camera as set forth in claim 14 wherein second predetermined angle is 35°–42°.

17. The fundus camera as set forth in claim 15 wherein said second predetermined angle is 39°.

18. The fundus camera as set forth in claim 17 wherein the outside diameter of said inside ring is 9mm, said outside ring is spaced apart a distance of 0.5mm from said inside ring and is 1mm thick.

19. The fundus camera as set forth in claim 11 wherein the contact lens has a geometric shape to produce the first predetermined angle and includes a separator over the fibers forming said inside ring with fibers forming said outside ring being positioned over said separator, said separator having an outer surface tapered to produce said second predetermined angle.

20. An ophthalmoscope comprising a contact lens I, a doublet comprised of lenses II and III spaced apart a distance $S_1$ from said lens I, lens II being a double convex lens in surface contact with a double concave lens III, a singlet double convex lens IV located a distance $S_2$ from lens III, a doublet comprised of two convex-concavo lens V and VI in surface contact and spaced apart a distance $S_3$ from lens IV, said lens having the following parameters:

| Lens | Radius, R | Thickness, T | Space, S | Refractive Index | Abbe number (dispersion) |
|---|---|---|---|---|---|
| I | $R_1$ = 8.2 mm<br>$R_2$ = 10.2 mm | $T_1$=9.2mm | 4.0 mm | 2.1 | 25.6 |
| II | $R_3$ =−3.0737 in<br>$R_4$ = 1.3780 in | $T_2$=12 mm | | 1.85026 | 32.23 |
| III | $R_5$ = 1.3780 in | $T_3$= 3 mm | $S_2$=5 mm | 1.5168 | 64.17 |
| IV | $R_6$ =−3.8189 in<br>$R_7$ = 1.5645 in | $T_4$=10 mm | $S_3$=4 mm | 1.4645 | 65.77 |
| V | $R_8$ = 4.3282 in<br>$R_9$ = 3.6830 in | $T_5$= 4 mm | | 1.5168 | 64.17 |
| VI | $R_{10}$=49.6846 in | $T_6$= 8 mm | | 1.7215 | 29.25. |

21. A lens series for use in conjunction with a 50mm focal length camera comprising a contact lens I, a doublet comprised of lenses II and III spaced apart a distacne $S_1$ from said lens I, lens II being a double convex lens in surface contact with a double concave lens III, a singlet plano-convex lens IV located a distance $S_2$ from lens III, a doublet comprised of a convex-concavo lens V in surface contact with a double concave lens IV spaced apart a distance $S_3$ from lens IV, said lens having the following parameters:

| Lens | Radius, R | Thickness, T | Space, S | Refractive Index | Abbe number (dispersion) |
|---|---|---|---|---|---|
| I | $R_1$= 8.2 mm<br>$R_2$= 10.2 mm | $T_1$=9.2 mm | | 2.1 | 25.6 |
| II | $R_3$ =1440. in<br>$R_4$ = 44.4 in | $T_2$=20mm | $S_1$=23mm | 1.85026 | 32.23 |
| III | $R_5$=−59.7 in | $T_3$= 6mm | $S_2$=30mm | 1.5168 | 64.17 |
| IV | $R_6$ = ∞<br>$R_7$ = 66.3 in | $T_4$=15mm | $S_3$=20mm | 1.4645 | 65.77 |
| V | $R_8$ = 165 in<br>$R_9$ = 169 in | $T_5$= 6mm | | 1.5168 | 64.17 |
| VI | $R_{10}$= 94.8 in | $T_6$=20mm | | 1.7215 | 29.25. |

* * * * *

UNITED STATES PATENT AND TRADEMARK OFFICE
CERTIFICATE OF CORRECTION

PATENT NO. : 3,944,341
DATED : March 16, 1976
INVENTOR(S) : Oleg Pomerantzeff

It is certified that error appears in the above-identified patent and that said Letters Patent are hereby corrected as shown below:

Column 1, line 51, change "comparitively" to --comparatively--.

Column 1, line 53, change "capaple" to --capable--.

Column 3, line 52, change "tranmit" to --transmit--.

Column 4, line 31, change "aperature" to --aperture--.

Column 4, line 49, change "forming" to --form--.

Column 6, line 4, before "points" insert --of--.

Column 7, line 15, before "radius" insert --a--.

Column 8, lines 33 and 34 (claim 3), delete "between the range".

Column 9, line 1 (claim 10), "Th" should be --The--.

Column 9, lines 34 and 35 (claim 13) delete "between the range".

Column 10, line 31 (claim 21), change "tacne" to --tance--.

Signed and Sealed this

Third Day of August 1976

[SEAL]

Attest:

RUTH C. MASON
Attesting Officer

C. MARSHALL DANN
Commissioner of Patents and Trademarks